United States Patent [19]

Liu

[11] Patent Number: 6,020,493
[45] Date of Patent: Feb. 1, 2000

[54] SINGLE-SITE CATALYST PREPARATION

[75] Inventor: Jia-Chu X. Liu, Mason, Ohio

[73] Assignee: Equistar Chemicals, LP, Houston, Tex.

[21] Appl. No.: 09/306,292

[22] Filed: May 6, 1999

[51] Int. Cl.[7] .................................................. C07F 9/80
[52] U.S. Cl. ..................................................... 546/7; 546/7
[58] Field of Search ..................................................... 546/7

[56] References Cited

U.S. PATENT DOCUMENTS

| 5,064,802 | 11/1991 | Stevens et al. | 502/155 |
| 5,539,124 | 7/1996 | Etherton et al. | 548/402 |
| 5,554,775 | 9/1996 | Krishnamurti et al. | 556/7 |
| 5,599,761 | 2/1997 | Turner | 502/152 |
| 5,637,660 | 6/1997 | Nagy et al. . | |
| 5,756,611 | 5/1998 | Etherton et al. | 526/127 |

FOREIGN PATENT DOCUMENTS

WO 96/34201  10/1996  WIPO .

OTHER PUBLICATIONS

M. J. Frazer and B. Rimmer, "Reactions of 8–Quinolinol with Covalent Halides. Part II. Tin (iv) and Titanium (iv) Halides," *J. Chem. Soc.*, Part A, (1968) 69.

M. J. Frazer and Z. Goffer, "Reactions of 8–Quinolinol with Covalent Halides. Part I. Tin and titanium Tefrachlorides," *J. Chem. Soc.*, Part A, (1966) 544.

*Primary Examiner*—John Kight
*Assistant Examiner*—Binta Robinson
*Attorney, Agent, or Firm*—Jonathan L. Schuchardt

[57] ABSTRACT

An improved method of making an olefin polymerization catalyst is disclosed. The method reacts essentially equimolar amounts of a Group 4 transition metal tetrahalide and a quinolinol or pyridinol in the presence of a $C_5$–$C_{10}$ hydrocarbon at a temperature within the range of about 0° C. to about 60° C. The method gives high yields of quinolinoxy or pyridinoxy-substituted Group 4 transition metal trihalides in a single reaction step. Particularly when combined with an activator, the target compounds are excellent olefin polymerization catalysts.

12 Claims, No Drawings

SINGLE-SITE CATALYST PREPARATION

FIELD OF THE INVENTION

The invention relates to the synthesis of single-site catalysts useful for olefin polymerizations. In particular, the invention relates to an improved way to make Group 4 transition metal catalysts that contain a quinolinyl or pyridinyl ligand.

BACKGROUND OF THE INVENTION

Interest in metallocene and non-metallocene single-site catalysts (hereinafter all referred to as single-site catalysts) continues to grow rapidly in the polyolefin industry. These catalysts are more reactive than Ziegler-Natta catalysts, and they produce polymers with improved physical properties. The improved properties include narrow molecular weight distribution, reduced low molecular weight extractables, enhanced incorporation of α-olefin comonomers, lower polymer density, controlled content and distribution of long-chain branching, and modified melt rheology and relaxation characteristics.

Recent attention has focused on developing improved single-site catalysts in which a cyclopentadienyl ring ligand of the metallocene is replaced by a heteroatomic ring ligand. For example, U.S. Pat. No. 5,554,775 discloses catalysts containing a boraaryl moiety such as boranaphthalene or boraphenanthrene. U.S. Pat. No. 5,539,124 discloses catalysts containing a pyrrolyl ring, i.e., an "azametallocene." In addition, PCT Int. Appl. WO 96/34021 discloses azaborolinyl heterometallocenes wherein at least one aromatic ring includes both a boron atom and a nitrogen atom.

Single-site catalysts that contain heteroatomic ring ligands ("heterometallocenes") are often quite challenging to synthesize. There continues to be a need for heterometallocenes that can be prepared inexpensively and in short order.

U.S. Pat. No. 5,637,660 discloses single-site catalysts that contain a Group 4 transition metal (such as titanium or zirconium) and at least one quinolinyl or pyridinyl group. When combined with an activator such as MAO or an ionic borate, these catalysts efficiently polymerize olefins such as ethylene or mixtures of ethylene and α-olefins. The ready availability of quinolinols and pyridinols and ease of preparation make these catalysts an attractive alternative to other heterometallocenes.

The '660 patent illustrates a relatively simple, two-step method for making the catalysts (see Example 3). First, the quinolinol or pyridinol reacts with an equivalent of butyllithium in toluene to give a slurry of the lithium quinolinolate or pyridinolate salt. The lithium salt is then combined with one molar equivalent of a Group 4 transition metal tetrahalide (e.g., titanium tetrachloride) to give the desired quinolinoxy or pyridinoxy-substituted transition metal trihalide. For example, the reaction of lithium 8-quinolinolate with an equimolar amount of titanium tetrachloride gives 8-quinolinoxytitanium trichloride. Unfortunately, the isolated yield of the desired transition metal catalyst is only 20–25%. Better yields are clearly needed.

Frazer et al. (J. Chem. Soc. (A) (1966) 544) disclose reactions of 8-quinolinol with covalent halides such as titanium or tin tetrahalides. Frazer found that "adducts" (rather than reaction products) are obtained when titanium tetrahalide is combined with one or two equivalents of 8-quinolinol at room temperature in chloroform. When two or more equivalents of 8-quinolinol are used, Frazer isolates a reaction product, which is primarily bis(8-quinolinoxy) titanium dichloride (see reaction scheme at column 1, page 545 of the reference). 8-Quinolinoxytitanium trichloride is made from the bis(8-quinolinoxy) compound by reacting the latter with an equimolar amount of titanium tetrachloride in chloroform.

In sum, an improved way to make single-site, heterometallocenes is needed. In particular, better ways to make heterometallocenes from readily available quinolinols and pyridinols would be valuable. Ideally, the method would be easy to practice and would give high yields of olefin polymerization catalyst precursors.

SUMMARY OF THE INVENTION

The invention is a method for making an olefin polymerization catalyst based on a quinolinol or pyridinol. The method comprises reacting essentially equimolar amounts of a Group 4 transition metal tetrahalide and a quinolinol or pyridinol in the presence of a $C_5$–$C_{10}$ hydrocarbon at a temperature within the range of about 0° C. to about 60° C. The resulting product is a quinolinoxy or pyridinoxy-substituted Group 4 transition metal trihalide.

I surprisingly found that the above method gives high yields (85% or more) of the desired quinolinoxy or pyridinoxy-substituted compounds in a single reaction step. The method overcomes the disadvantages of earlier processes, which use multiple steps and/or lithium salt intermediates, and give low yields of the target compounds. When combined with an activator, the quinolinoxy and pyridinoxy-substituted Group 4 transition metal trihalides are excellent olefin polymerization catalysts.

DETAILED DESCRIPTION OF THE INVENTION

In the method of the invention, essentially equimolar amounts of a a Group 4 transition metal tetrahalide and a quinolinol or pyridinol react to produce a quinolinoxy or pyridinoxy-substituted Group 4 transition metal trihalide.

By "essentially equimolar amounts," we mean a proportion of the two key reactants that gives the desired quinolinoxy or pyridinoxy-substituted metal trihalide as the major reaction product. Preferably, "essentially equimolar" means a relative mole ratio within the range of about 0.9 to about 1.1 moles, more preferably from about 0.95 to about 1.05 moles, of Group 4 transition metal tetrahalide per mole of quinolinol or pyridinol.

A Group 4 transition metal tetrahalide is used in the method. Group 4 transition metals are titanium, zirconium, and hafnium. Suitable tetrahalides include tetrachlorides, tetrabromides, and tetraiodides, with tetrachlorides being most preferred. Mixed tetrahalides, such as dichlorodibromozirconium or trichlorobromotitanium, are also suitable. Mixtures of different Group 4 transition metal compounds can also be used, such as a mixture of titanium tetrachloride and zirconium tetrachloride.

The metal tetrahalide reacts with a quinolinol or pyridinol. Suitable quinolinols and pyridinols have a nitrogen-containing, six-membered aromatic ring (a pyridine ring) and a hydroxyl group attached to the pyridine ring (as in 2-pyridinol) or to an aromatic ring that is fused to the pyridine ring (as in 8-quinolinol). Either ring can have one or more substituent groups, including halogens, nitro groups, alkyls, aryls, or the like. Suitable pyridinols include, for example, 2-pyridinol, 3-pyridinol, 4-pyridinol, 5-chloro-2-pyridinol, 5-methyl-2-pyridinol, 4-nitro-2-pyridinol, and the like. 2-Pyridinol is particularly preferred. Suitable quinolinols include, for example, 8-quinolinol, 7-quinolinol, 6-quinolinol, 5-quinolinol, 4-quinolinol, 3-quinolinol, 2-quinolinol, 5-methyl-8-quinolinol, 4-nitro-8-quinolinol, 2,7-dichloro-8-quinolinol, and the like.

The method of the invention is performed in the presence of a $C_5$–$C_{10}$ hydrocarbon. Suitable hydrocarbons are aromatic and aliphatic hydrocarbons, with linear, branched, and cyclic aliphatic hydrocarbons being particularly preferred. Suitable hydrocarbons include, for example, benzene, toluene, xylenes, pentanes, hexanes, heptanes, octanes, nonanes, decanes, and the like, and mixtures thereof. Particularly preferred are $C_6$–$C_8$ aliphatic hydrocarbons such as hexanes, heptanes, and octanes, and mixtures thereof.

The amount of hydrocarbon needed depends on a number of factors, including the identity of the hydrocarbon, the desired reaction rate, the solubility of the reactants, the solubility of the reaction products, the reaction temperature, and other variables.

The method is performed at a temperature within the range of about 0° C. to about 60° C. At temperatures lower than 0° C., the transition metal tetrahalide often has insufficient solubility, which can lead to an undesirable distribution of products (usually too much of the bispyridinyl or bisquinolinyl compound). Temperatures above 60° C. are undesirable because the reaction products tend to disproportionate to give a mixture of compounds. More preferably, a reaction temperature within the range of about 25° C. to about 45° C. is used. In one particularly preferred method, the reactants are combined at about 30° C. to about 40° C., and are then stirred at about room temperature until the reaction is complete.

The reaction product is a quinolinoxy or pyridinoxy-substituted Group 4 transition metal trihalide. Examples include 8-quinolinoxytitanium trichloride, 2-pyridinoxytitanium trichloride, 2-pyridinoxyzirconium trichloride, 7-quinolinoxyhafnium tribromide, 4-pyridinoxyzirconium triiodide, and the like, and mixtures thereof.

The reactants can be combined in any desired order or manner. In one convenient method, the quinolinol or pyridinol is dissolved or suspended in the hydrocarbon at or slightly above room temperature and is stirred under an inert atmosphere such as nitrogen or argon. The Group 4 transition metal tetrahalide is then preferably added, usually as a solution or suspension in more of the hydrocarbon. After stirring the reaction mixture awhile, preferably at room temperature, solvents are removed, and the residual product is recovered, washed, and recrystallized if desired from a suitable solvent.

I surprisingly found that the simple method described above gives excellent yields (85% or more) of the desired pyridinoxy or quinolinoxy-substituted Group 4 transition metal trihalide in a single reaction step. The method overcomes the disadvantages of earlier synthetic routes, which use multiple steps and/or lithium salt intermediates, and give low yields of the target compounds. In particular, the need to produce a lithium salt of the pyridinol or quinolinol as shown in U.S. Pat. No. 5,637,660 is avoided (see Comparative Example 1 below). In addition, the process avoids the need to use a multistep method via a bis(quinolinoxy) or bis(pyridinoxy) intermediate as taught by Frazer (see Background).

When combined with an optional activator, the quinolinoxy and pyridinoxy-substituted Group 4 transition metal trihalides are excellent olefin polymerization catalysts.

Generally, the activator converts the complex to a cationically active species. The catalysts are especially valuable for polymerizing olefins. Suitable olefins include ethylene, propylene, butenes, pentenes, hexenes, octenes, styrenes, 1,3-butadiene, norbornene, and the like. Preferred olefins are ethylene, propylene, and mixtures thereof with α-olefins such as 1-butene, 1-hexene, and 1-octene.

Suitable activators are well known in the art. Examples include alumoxanes (methyl alumoxane (MAO), PMAO, ethyl alumoxane, diisobutyl alumoxane), alkylaluminum compounds (triethylaluminum, diethylaluminum chloride, trimethylaluminum), and the like. Suitable activators include acid salts that contain non-nucleophilic anions. These compounds generally consist of bulky ligands attached to boron or aluminum. Examples include lithium tetrakis(pentafluorophenyl) borate, lithium tetrakis (pentafluorophenyl) aluminate, anilinium tetrakis (pentafluorophenyl) borate, and the like. Suitable activators also include trialkyl or triarylboron compounds such as tris(pentafluorophenyl)boron, tris(pentabromophenyl) boron, and the like. Other suitable activators are described, for example, in U.S. Pat. Nos. 5,756,611, 5,064,802, and 5,599,761, the teachings of which are incorporated herein by reference.

The catalysts are optionally used with an inorganic solid or organic polymer support. Suitable supports include silica, alumina, silica-aluminas, magnesia, titania, clays, zeolites, or the like. The supports can be pretreated thermally or chemically to improve catalyst productivity or product properties. The catalysts can be deposited on the support in any desired manner. For instance, the catalyst can be dissolved in a solvent, combined with a support, and stripped. Alternatively, an incipient-wetness technique can be used. Moreover, the support can simply be introduced into the reactor separately from the catalyst.

The catalysts can be used in a variety of well-known olefin polymerization processes, including gas, high-pressure liquid, slurry, solution, or suspension-phase techniques, and combinations of these.

The following examples merely illustrate the invention. Those skilled in the art will recognize many variations that are within the spirit of the invention and scope of the claims.

EXAMPLE 1

Preparation of 8-Quinolinoxytitanium Trichloride

8-Quinolinol (1.45 g, 0.010 mol) is added to a three-neck flask with heptane (30 mL), and the mixture is stirred under nitrogen at 25 to 40° C. for 0.5 h. It becomes a pale yellow suspension. Titanium tetrachloride (10 mL of 1.0 M solution in heptane, 0.010 mol) is added dropwise to the suspension. After stirring at 25° C. for 2 h, solvents are removed under vacuum. The product is washed with heptane (30 mL), and the washings are decanted. The residue is dried under vacuum for 1 h, and is then recrystallized from a mixture of hydrocarbon solvents to give purple crystals of 8-quinolinoxytitanium trichloride (2.85 g, 95%).

COMPARATIVE EXAMPLE 1

Preparation of 8-Quinolinoxytitanium Trichloride from Lithium Salt

8-Quinolinoxytitanium trichloride is made by the method of U.S. Pat. No. 5,637,660. Thus, a slurry of lithium 8-quinolinolate in toluene (30 mL) (prepared by reacting 1.45 g of 8-quinolinol (0.010 mol) with an equimolar amount of methyllithium) is added at −78° C. to a stirred solution of titanium tetrachloride (1.9 g, 0.010 mol) in toluene (20 mL). The mixture is then allowed to warm to room temperature, and is stirred overnight. The resulting precipitate is isolated, washed with toluene, and is extracted into dichloromethane (100 mL). Removal of dichloromethane gives a brown, microcrystalline solid (0.7 g, 23%).

This example and Example 1 show that a far superior yield of the desired 8-quinolinoxytitanium trichloride is available by using the method of the invention versus using a well-known synthetic alternative.

EXAMPLES 2–4

Preparation of Other Quinolinoxytitanium Trichlorides

The procedure of Example 1 is followed to prepare the quinolinoxytitanium trichlorides from 6-quinolinol, 5-quinolinol, and 4-quinolinol. The yields are as follows: 6-quinolinoxytitanium trichloride: 2.85 g (96%); 5-quinolinoxytitanium trichloride: 2.88 g (97%); 4-quinolinoxytitanium trichloride: 2.90 g (97%). The examples demonstrate the reliability of the method of the invention for making other quinolinols.

EXAMPLE 5

Preparation of 2-Pyridinoxytitanium Trichloride

The method of Example 1 is used, except that 2-pyridinol (0.951 g, 0.010 mol) is used in place of 8-quinolinol. The product obtained is 2-pyridinoxytitanium trichloride (2.40 g, 97%). When the same product is made by the method of Comparative Example 1, the yield is much lower (0.50 g, 20%).

EXAMPLE 6

Preparation of 3-Pyridinoxytitanium Trichloride

The method of Example 1 is used, except that 3-pyridinol (0.951 g, 0.010 mol) is used in place of 8-quinolinol. The product obtained is 3-pyridinoxytitanium trichloride (2.38 g, 96%). When the same product is made by the method of Comparative Example 1, the yield is much lower (0.50 g, 20%).

EXAMPLE 7

Preparation of 4-Pyridinoxytitanium Trichloride

The method of Example 1 is used, except that 4-pyridinol (0.951 g, 0.010 mol) is used in place of 8-quinolinol. The product obtained is 4-pyridinoxytitanium trichloride (2.41 g, 97%). When the same product is made by the method of Comparative Example 1, the yield is much lower (0.48 g, 19%).

Examples 5–7 demonstrate that a far superior yield of the desired pyridinoxytitanium trichloride is available by using the method of the invention versus using a well-known synthetic alternative.

The preceding examples are meant only as illustrations. The following claims define the invention.

I claim:

1. A method which comprises reacting essentially equimolar amounts of a Group 4 transition metal tetrahalide and a quinolinol or pyridinol in the presence of a $C_5$–$C_{10}$ hydrocarbon at a temperature within the range of about 0° C. to about 60° C. to produce a quinolinoxy or pyridinoxy-substituted Group 4 transition metal trihalide.

2. The method of claim 1 wherein the Group 4 transition metal halide is added to the quinolinol or pyridinol.

3. The method of claim 2 wherein the addition is performed at a temperature within the range of about 25° C. to about 45° C.

4. The method of claim 1 wherein the Group 4 transition metal halide is titanium tetrachloride.

5. The method of claim 1 wherein the quinolinol is an 8-quinolinol.

6. The method of claim 1 wherein the pyridinol is a 2-pyridinol.

7. The method of claim 1 wherein the hydrocarbon is selected from the group consisting of hexanes, heptanes, octanes, and mixtures thereof.

8. A method which comprises adding a quinolinol or pyridinol to an essentially equimolar amount of a Group 4 transition metal tetrahalide in the presence of a $C_6$–$C_8$ hydrocarbon at a temperature within the range of about 25° C. to about 45° C. to produce a quinolinoxy or pyridinoxy-substituted Group 4 transition metal trihalide.

9. The method of claim 8 wherein the Group 4 transition metal tetrahalide is titanium tetrachloride.

10. The method of claim 8 wherein the quinolinol is an 8-quinolinol.

11. The method of claim 8 wherein the pyridinol is a 2-pyridinol.

12. The method of claim 8 wherein the hydrocarbon is heptane.

* * * * *